United States Patent [19]

Göschke

[11] Patent Number: 4,624,951
[45] Date of Patent: Nov. 25, 1986

[54] SUBSTITUTED PYRIDAZINONES, PHARMACEUTICAL PREPARATIONS CONTAINING THESE COMPOUNDS, AND THE USE THEREOF

[75] Inventor: Richard Göschke, Bottmingen, Switzerland

[73] Assignee: Ciba-Geigy Corporation, Ardsley, N.Y.

[21] Appl. No.: 817,804

[22] Filed: Jan. 10, 1986

Related U.S. Application Data

[63] Continuation of Ser. No. 764,286, Aug. 12, 1985, abandoned.

[30] Foreign Application Priority Data

Aug. 17, 1984 [CH] Switzerland ............... 3945/84

[51] Int. Cl.⁴ ............... A61K 31/535; C07D 413/10
[52] U.S. Cl. .................... 514/234; 514/236; 514/237; 514/238; 514/240; 544/114
[58] Field of Search ............... 544/114; 514/234, 236, 514/237, 238, 240

[56] References Cited

U.S. PATENT DOCUMENTS 3,689,652  9/1972  Curran et al. ............. 424/250
3,746,712  7/1973  Ross et al. ............. 260/250 A
3,812,256  5/1974  Curran ............. 424/250
3,975,388  8/1976  Hakim et al. ............. 544/114
4,088,762  5/1978  Abdulhameed et al. ............. 424/250

FOREIGN PATENT DOCUMENTS 0129791  1/1985  European Pat. Off. .

Primary Examiner—Robert W. Ramsuer
Attorney, Agent, or Firm—Michael W. Glynn; Irving M. Fishman

[57] ABSTRACT

The present invention relates to novel substituted pyridazinones of the general formula I

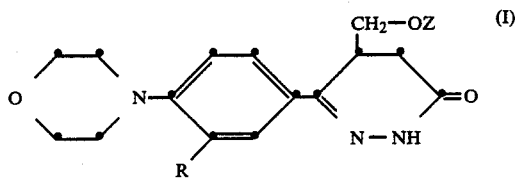

wherein R is a halogen atom, a lower alkyl or lower alkoxy group, the nitro, hydroxyl, cyano, carboxyl, lower alkoxycarbonyl or carbamoyl group or the trifluoromethyl group, and Z is hydrogen or an acyl group, and the salts and tautomeric forms thereof, which have a marked antithrombotic action, to the production of these novel compounds, to pharmaceutical preparations containing them, and to their use.

10 Claims, No Drawings

SUBSTITUTED PYRIDAZINONES, PHARMACEUTICAL PREPARATIONS CONTAINING THESE COMPOUNDS, AND THE USE THEREOF

This application is a continuation of application Ser. No. 764,286, filed Aug. 12, 1985, now abandoned.

The present invention relates to novel substituted pyridazinones, particularly 5-hydroxymethyl-4,5-dihydro-3(2H)-pyridazinones, to the production thereof, to pharmaceutical preparations containing these novel compounds, and to their use.

It has now been found that the novel compounds of the general formula I

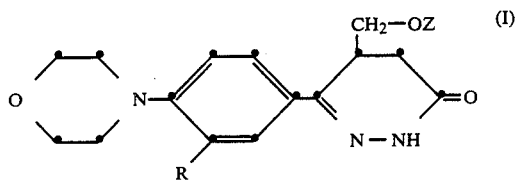

wherein R is a halogen atom, a lower alkyl or lower alkoxy group, the nitro, hydroxyl, cyano, carboxyl, lower alkoxycarbonyl, carbamoyl or trifluoromethyl group, and Z is hydrogen or an acyl group, as well as their salts and their tautomeric forms, surprisingly have a marked antithrombotic action.

The term "lower" defines in the organic radicals or compounds given above or in the following those having at most 7, preferably 4, and in particular 1 or 2, carbon atoms.

As lower alkyl, R is for example: ethyl, propyl, isopropyl, butyl, isobutyl or tert-butyl, and especially methyl; as lower alkoxy, it is for example: ethoxy, propoxy, isopropoxy, butoxy, isobutoxy and particularly methoxy; and as halogen, it is bromine, iodine, especially fluorine and in particular chlorine.

As lower alkoxycarbonyl, R is for example the methoxycarbonyl or ethoxycarbonyl group.

As acyl, Y is the radical of an organic carboxylic acid, for example lower alkanoyl, such as acetyl, propionyl or butyryl; halo-lower-alkanoyl, for example acetyl, such as chloroacetyl; or aroyl, for example benzoyl. The phenyl radical in the benzoyl group is unsubstituted or mono- or polysubstituted by halogen, lower alkyl, lower alkoxy, hydroxyl, nitro, carboxyl or trifluoromethyl.

The compounds of the formula I have valuable pharmacological properties. They thus exhibit for example a pronounced antithrombotic action. This can be demonstrated for example on the guinea pig by virtue of the suppression of thrombocytopenia after induction by means of ADP (Thromboembolism, Edited by J. R. Mitchell and J. G. Doment, Academic Press (1977), p. 36) in the dose range of about 30 to 300 mg/kg p.o., on the basis of the Forssman reaction (Thrombosis, Haemostasis 42, 100 (1979)) in the dose range of about 100 to 300 mg/kg p.o., and on the basis of the suppression of the thrombosis forming on a cotton thread in an extracorporeal shunt on the rat (method analogous to Brit. J. Pharmacol., 73. 219 P (1981)) in the dose range of about 5 to 50 mg/kg p.o., as well as by virtue of the suppression of the platelet aggregation, induced ex vivo by collagen or arachidonic acid, after prior peroral administration of the active substance in doses of 5 to 100 mg/kg. The compounds of the general formula I are accordingly excellently suitable for the treatment of thrombotic diseases, and can be used as active ingredients in antithrombotic pharmaceutical preparations.

The invention relates in particular to compounds in which R is a halogen atom, the cyano, hydroxyl, carboxyl, lower alkyl, lower alkoxy or trifluoromethyl group, and Z is hydrogen or lower alkanoyl, and also to the salts and the tautomeric forms of these compounds.

Of particular interest in this invention are compounds in which R is a halogen atom, especially chlorine, a lower alkyl group, particularly methyl, or the cyano group, and Z is hydrogen or lower alkanoyl, especially acetyl, and the tautomeric forms thereof.

The compounds of the formula I and their tautomeric forms which are described in the Examples subsequently given are to be mentioned in particular.

The novel pyridazinones of the formula I are produced by methods known per se.

The novel compounds of the formula I can thus be obtained by reacting a ketocarboxylic acid of the formula II

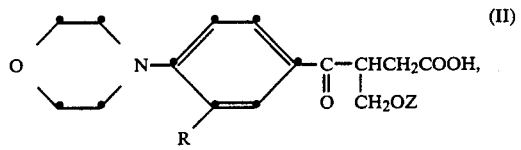

or a reactive derivative of such a ketocarboxylic acid, wherein R and Z have the meanings defined in the foregoing, with hydrazine. There is preferably used hydrazine hydrate in hydrate form, which when used in excess can simultaneously also serve as solvent. It is however more advantageous to add an additional inert solvent. Suitable inert solvents are preferably alcohols, for example: methanol, ethanol, isopropanol, n-butanol, isoamyl alcohol, glycols and ethers thereof, such as ethylene glycol, diethylene glycol, ethylene glycol monomethyl or -monoethyl ether (methyl glycol or ethyl glycol), also ethers, especially water-soluble ethers, such as tetrahydrofuran, dioxane or ethylene glycol dimethyl ether (diglymes), and also water; as well as mixtures of these solvents with one another, particularly mixtures with water, for example aqueous ethanol. The reaction temperatures are advantageously between about 20° and about 200° C., preferably between 60° and 80° C.

Suitable reactive derivatives of the ketocarboxylic acid of the formula II are for example the esters, in particular lower alkyl esters, such as methyl or ethyl ester. It is also possible to use the acid amides and acid halides of acids of the formula II, especially the acid chlorides or acid bromides. Especially suitable are lactones of the formula IIa

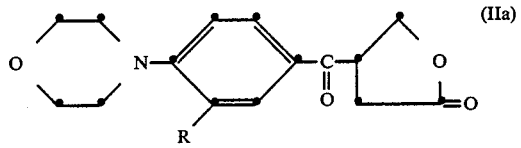

for reaction with hydrazine or a hydrazine hydrate.

Further suitable reactive derivatives of the carboxylic acid of the formula II can be formed in situ during the reaction. These include for example the hydrazones of the formula $R_1—C(=N—NH_2)—CH—(—CH_2—OZ)—CH_2—COOH$, the hydrazides of the formula $R_1—CO—CH(—CH_2—OZ)—CH_2—CO—NH—NH_2$, and the hydrazones of the hydrazides of the formula $R_1—C(=N—NH_2)—CH(—CH_2—OZ)—CH_2—CO—NH—NH_2$
wherein $R_1$ is the radical

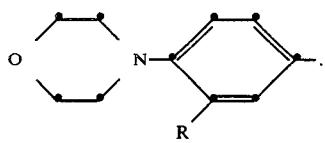

The starting materials formed in situ are produced from the ketocarboxylic acids of the formula II, and are not isolated from the reaction mixture but further reacted to the compounds of the formula I.

The compounds of the formula I can be obtained also by reacting compounds of the formula III

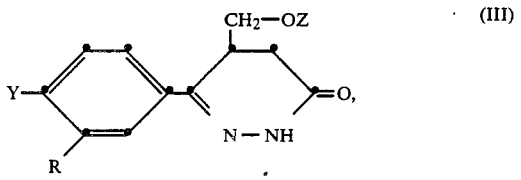

wherein R and Z have the meanings defined under the formula I, and Y is a group detachable together with hydrogen, with morpholine. The employed morpholine is advantageously used as a free base in excess; it can however also be used in the form of an acid addition salt, for example as a hydrohalide, such as hydrochloride.

With the use of only a slight excess of morpholine as a free base, or with the use of the morpholine as an acid addition salt, it is advantageous to additionally add a stoichiometrically equivalent amount of for example a tertiary alkylamine, such as triethylamine or N-ethyldiisopropylamine.

The described reaction of compounds of the formula III with morpholine is performed optionally in the presence of a solvent, preferably an aprotic solvent. Examples of solvents preferably used are ethers, for example diethyl ether and tetrahydrofuran, especially aliphatic ketones and esters, such as acetone, methyl ethyl ketone and ethyl acetate, aromatic hydrocarbons, for example benzene, toluene or xylene, as well as acetonitrile. The reaction is carried out particularly preferably in diethyl ether or acetonitrile.

The reactions can be performed at a temperature of between 0° and 150° C., preferably however between room temperature and the reflux temperature of the reaction mixture.

A group Y detachable together with hydrogen is for example in particular a free or preferably etherified mercapto group, also an optionally reactive, functionally modified hydroxyl group or the nitroamino group. An etherified mercapto group is especially a mercapto group etherified by an unsubstituted or substituted hydrocarbon, particularly one of aliphatic character. It is especially lower alkylthio, for example methylthio, ethylthio or butylthio, also phenylthio or phenyl-lower-alkylthio, for example benzylthio. An optionally reactive functionally modified hydroxyl group is a free hydroxyl group and, inter alia, a corresponding esterified hydroxyl group. Such a group is, inter alia, halogen, for example chlorine or bromine, or lower alkylsulfonyloxy, for example methanesulfonyloxy.

As a group detachable together with hydrogen, Y is preferably a halogen atom, for example chlorine or bromine.

Compounds of the general formula I can be produced also by reacting a compound of the formula IV

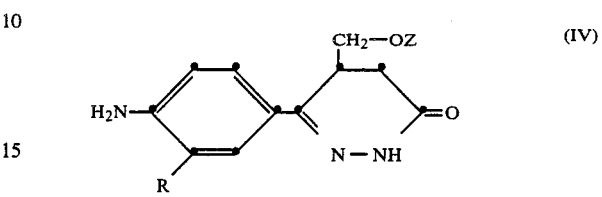

with a diethyl ether derivative of the formula V

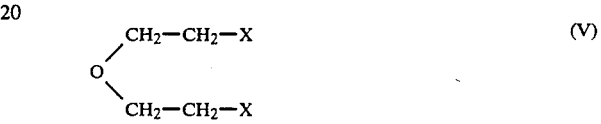

wherein X is a group detachable together with hydrogen, and R and Z have the meanings defined in the foregoing.

The reaction of a compound of the formula IV with a compound of the formula V is performed preferably in the presence of an organic base, for example a tertiary alkylamine, such as triethylamine or N-ethyldiisopropylamine.

The described reaction of compounds of the formula IV with a compound of the formula V is performed optionally in the presence of a solvent, preferably a polar solvent, for example dimethylformamide.

The reactions can be carried out at a temperature of between 0° and 200° C., preferably however between room temperature and the reflux temperature of the reaction mixture.

A group X detachable together with hydrogen has already been defined above for the symbol Y under the formula III.

As a group detachable together with hydrogen, X is preferably a halogen atom, for example chlorine or bromine.

According to a further process, compounds of the formula I wherein R is a halogen atom or the cyano group can be produced by heating a compound of the formula VI

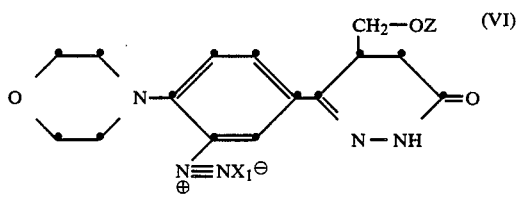

wherein $X_1^\ominus$ is an anion of a mineral acid, for example in the presence of copper or of a copper-I salt, for example a halide or cyanide. An anion of a mineral acid is for example the anion of a hydrohalic acid. In the case of the introduction of R as fluorine, $X_1^\ominus$ is a fluoride or tetrafluoroborate anion. The heating of a compound of the formula VI where X is a fluoride or tetrafluoroborate anion is performed in hydrofluoric acid or in tetrafluoroboric acid. With the introduction of a cyano group, the diazonium salt of the formula VI is for example reacted with copper-I cyanide, which is present as a complex with potassium cyanide in solution. For example, a diazonium salt of the formula VI is reacted with a mixture of potassium cyanide and copper-I sulfate.

The liberation of the diazonium salt is effected thermally at temperatures of between 30° and 150° C., preferably between 30° and 40° C. when a diazonium fluoride is present, and between 100° and 150° C. when a diazonium tetrafluoroborate is present.

The diazotisation of aromatic amines is performed for example with an alkali metal nitrite, such as sodium nitrite, preferably with the aid of anhydrous sodium nitrite. Diazotisation is performed for example at a temperature of between −10° and −10° C., preferably at a temperature of between 0° and 5° C. By reaction with a mineral acid, there are obtained compounds of the formula VI in which $X_1$ is the anion of a mineral acid.

By use of a further process, compounds of the formula I wherein R is a halogen atom can be produced by halogenating compounds of the formula VII

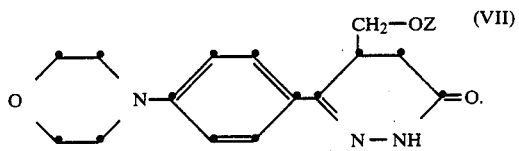

Halogenation can be performed on the one hand by the use of halogen, preferably in the presence of a Lewis acid, for example in the presence of an iron-III, aluminium, antimony-III or tin-IV halide; and on the other hand by means of a halogen carrier, for example in the presence of a heavy metal, such as iron, or with the use of a halogenating agent, for example hydrogen chloride, in the presence of an oxidising agent, for example hydrogen peroxide, or of an alkali metal chlorate, for example sodium chlorate, of a nitrosyl halide, for example nitrosyl chloride or bromide, or of an N-halo-imide, for example bromosuccinimide and -phthalimide.

The direct introduction of an iodine atom is performed with the use of hydrogen iodide in the presence of an oxidising agent, for example in the presence of nitric acid or mercury oxide.

The halogenation reactions mentioned are performed, depending on the halogen atom concerned, at temperatures of between −10° C. and the reflux temperature of the reaction mixture, preferably at a temperature of between −5° and +30° C.

Compounds of the formula I in which R has the meanings defined under the formula I, and Z is hydrogen, can be obtained also by solvolysing or hydrogenolysing a compound of the formula VIII

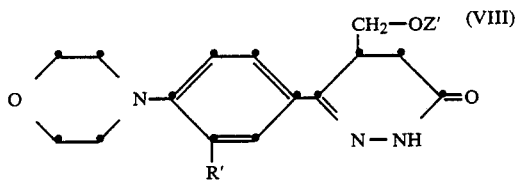

wherein R' has the meaning of R, or is a readily solvolysable or hydrogenolysable ether group or acyloxy group, and —OZ' is a readily solvolysable or hydrogenolysable ether or acyloxy group.

An ether or acyloxy group which can be readily solvolysed or hydrogenolysed is for example an ether or acyloxy group which is detachable by solvolysis, including hydrolysis, acidolysis or alcoholysis, or by means of reduction, including hydrogenolysis.

An acyloxy group R' or —OZ' detachable by solvolysis is for example an acyloxy group in which the acyl moiety is the radical of an organic carboxylic acid, for example lower alkanoyl, such as acetyl, halo-lower-alkanoyl, such as haloacetyl, for example chloroacetyl, or carbamoyl, or aroyl, such as benzoyl, also the acyl moiety is the radical of a semi-ester of carbonic acid, such as lower-alkoxycarbonyl, for example methoxycarbonyl, ethoxycarbonyl or tert-butyloxycarbonyl, 2-halo-lower-alkoxycarbonyl, for example 2,2,2-trichloroethoxycarbonyl or 2-iodoethoxycarbonyl, unsubstituted or substituted 1-phenyl-lower-alkoxycarbonyl, for example benzyloxycarbonyl or diphenylmethoxycarbonyl or aroylmethoxycarbonyl, for example phenacyloxycarbonyl, also an unsubstituted or substituted 1-polyphenyl-lower-alkyl group, wherein substituents of the phenyl moiety can be for example lower alkyl or lower alkoxy, for example methyl or methoxy, and in particular trityl, or an organosilyl radical, especially trimethylsilyl.

An ether group detachable by solvolysis is for example lower alkoxy, for example methoxy or ethoxy, or a 1-phenyl-lower-alkoxy group, such as benzyloxy. These radicals can be substituted by lower alkoxy, for example methoxy or ethoxy, or lower alkoxyethoxy, for example methoxyethoxy.

Benzyloxy radicals as detachable ether groups can be unsubstituted or substituted by one or more substituents, for example lower alkyl, such as methyl, ethyl, isopropyl or n-propyl, halogen, for example chlorine or bromine, or lower alkoxy, for example methoxy or ethoxy. These substituents are situated preferably in the ortho-position or in the para-position.

Likewise detachable by solvolysis, particularly by hydrolysis or alcoholysis, in an acid medium are aliphatic ether groups substituted for their part in the α-position by an ether group, such as ethoxymethoxy, butoxymethoxy or 1-ethoxyethoxy, and especially analogous cyclic radicals, for example 1-oxacycloalkan-2-yloxy groups, in particular tetrahydropyran-2-yloxy, also for example 4-methoxytetrahydropyran-4-yloxy.

When the solvolysis of the ether or acyloxy groups R' and/or —OZ' is performed by hydrolysis, this is carried out, depending on the nature of the detachable groups, in the presence of an organic acid, such as p-toluenesulfonic acid, or of a mineral acid, such as hydrochloric acid or sulfuric acid, or in the presence of a hydroxide or carbonate of an alkali metal or alkaline-earth metal, or in the presence of ammonia or of an amine, such as isopropylamine, or hydrazine hydrate. If solvolysis is performed by means of one of the above-mentioned acids in an alcohol, for example by means of p-toluenesulfonic acid in ethyl alcohol, solvolysis is performed by alcoholysis.

Ether groups, for example lower alkoxy groups, in particular methoxy or ethoxy, can be detached in solution or in the melt by means of a metal halide, such as aluminium halide or boron halide, for example aluminium trichloride, aluminium tribromide, boron trichloride or boron tribromide. Suitable solvents are for example benzene, nitrobenzene or ethylene chloride (cf.

Jour. Chem. Soc. (1961), 1008; Ber. (1943), 76B, 900; Jour. Org. Chem. (1962), 27, 2037; Ber. (1960), 92, 2761; Jour. Am. Chem. Soc. (1968), 24, 2289; and Tetr. Lett. (1966), 4155).

Acyloxy groups detachable by acidolysis are those in which the acyl moiety is an acyl radical of semi-esters of carbonic acid, for example tert-lower-alkoxycarbonyl or unsubstituted or substituted diphenylmethoxycarbonyl. Also ether groups, for example tert-lower-alkoxy groups, can be detached by acidolysis. Detachment by acidolysis can be performed by treatment with suitable strong organic carboxylic acids, such as lower alkanecarboxylic acids unsubstituted or substituted by halogen, especially by fluorine, particularly trifluoroacetic acid (if necessary in the presence of an activating agent, such as anisole), as well as with formic acid. Where no prior mention is made, the above reactions are performed in the presence of a solvent or solvent mixture, suitable reactants also being able to act as such.

An ether group detachable by reduction, especially by hydrogenolysis, is in particular an α-aryl-lower-alkyl group, such as an unsubstituted or substituted 1-phenyl-lower-alkyl group, wherein lower alkyl has up to 7 carbon atoms, and wherein substituents, especially of the phenyl moiety, can be for example lower alkyl or lower alkoxy each having up to 7 carbon atoms, for example methyl or methoxy, and more especially however benzyl.

The reductive detachment of the ether groups can be performed in particular for example by treatment with catalytically activated hydrogen, such as hydrogen in the presence of a suitable hydrogenating catalyst, for example a nickel, platinum or palladium catalyst, and also a rhodium or ruthenium catalyst; or the process is performed with a hydride-reducing agent, for example lithium aluminium hydride.

By acyloxy radicals detachable by hydrogenolysis are meant those groups which are detached by treatment with a chemical reducing agent (especially with a reducing metal or a reducing metal compound). Such radicals are in particular 2-halo-lower-alkoxycarbonyloxy, such as 2,2,2-trichloroethoxycarbonyloxy, which are detached for example with a reducing heavy metal, for example zinc, or with a reducing heavy metal salt, such as a chromium(II) salt, for example chromium(II) chloride or -acetate, usually in the presence of an organic carboxylic acid, such as formic acid or acetic acid.

The above reduction reactions are performed in a manner known per se, usually in the presence of an inert solvent and, if necessary, with cooling or heating, for example in a temperature range of about −20° to about 150° C., and/or in a closed vessel under pressure.

Depending on the ether or acyloxy group present, there is preferably selected the mildest of the described solvolysis or hydrogenolysis methods, in order to avoid changes in the pyridazinone structure.

Within the limits of the definition of the final products, substituents can be introduced, modified or detached in the compounds of the formula I obtained.

For example, resulting compounds of the formula I wherein R is a hydroxyl group can be converted, in a manner known per se, by transesterification or by etherification into compounds of the formula I in which R is a halogen atom or a methoxy group.

The methods described can be performed, in a customary manner, at room temperature, with cooling or heating, under normal or elevated pressure and, if necessary, in the presence or absence of a diluent, catalyst or condensation agent. The reaction can, if required, also be carried out in an inert-gas atmosphere, for example in nitrogen.

The starting materials are known, or, where they are new, can be produced by methods known per se. In cases in which it appears to be of advantage, the employed starting products have already been defined after the description of the process.

Ketocarboxylic acids of the formula II can be produced using methods known per se, in the case for example of compounds of the formula II in which R is a halogen atom or a cyano group by halogenation or introduction of a cyano group in a compound of the formula X

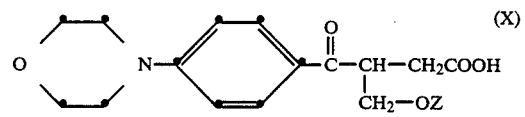

by the above-described methods, which are carried out in an analogous manner.

The lactones of the formula IIa used as derivatives can be obtained from the 3-(4-morpholino-benzoyl)-propionic acid correspondingly substituted by the substituent R by reaction with formaldehyde according to "Synthesis", Georg Thieme Verlag (October 1980), pp. 825–827.

Compounds of the general formula III are known, or they can be obtained, using the method described by J. D. Albright at al., J. Het. Chem. 15, 881 (1978), from the corresponding ketocarboxylic acid by reaction with hydrazine. It is also possible to obtain in an analogous manner the starting compounds of the general formula IV from the corresponding aminoketocarboxylic acids. Also the starting compounds of the general formula V are known, and can be obtained for example from the corresponding dihydroxydiethyl ethers by esterification with an acid, for example a hydrohalic acid. Diethyl ether derivatives of the formula V can also be obtained from the correspondingly substituted alcohols of the formula OH—CH₂—CH₂—X by etherification.

The starting compound of the formula VI can be produced from the corresponding nitro compound by reduction into the amino compound, and subsequent diazotisation.

Compounds of the general formula VIII can be obtained, using the method described in the first process, from the corresponding ketocarboxylic acids by reaction with hydrazine.

The invention relates also to those embodiments of a process in which a process is discontinued at some stage, or in which a compound obtainable as an intermediate at any stage is used as the starting material and the uncompleted stages are carried out, or in which a starting material is formed under the reaction conditions or, if required, is used in the form of a salt. The invention also includes novel intermediates resulting therefrom.

Also embraced by the invention are therapeutic compositions consisting of an antithrombotically active proportion of a compound of the formula I together with a pharmacologically acceptable solid carrier or liquid diluent.

A resulting compound of the formula I wherein R is a carboxyl group can be converted into a salt, in a manner known per se, for example by reaction with an approximately stoichiometric amount of a suitable salt-forming agent, such as ammonia, an amine, or a hydroxide, carbonate or hydrogen carbonate of an alkali metal or alkaline-earth metal. Ammonium or metal salts obtainable in this manner can be converted into the free acid by treatment with an acid, for example hydrochloric acid, sulfuric acid or acetic acid, until the required pH value is obtained.

The acid addition salts of the novel compounds of the invention can be converted, in a manner known per se, into the free compounds, for example with basic agents, such as alkalies or ion-exchangers. On the other hand, the free bases obtained can form salts with organic or inorganic acids.

The pharmaceutical preparations according to the invention contain at least one compound of the formula I as active ingredient, together with a customary pharmaceutical carrier. The nature of the carriers used is governed largely by the field of application. The pharmaceutical compositions according to the invention, which contain compounds of the formula I as active ingredients, can be administered orally, parenterally or rectally.

Suitable for the oral treatment of thrombosis are in particular solid dosage units, such as tablets, dragées and capsules, which preferably contain between 10 and 90% of an active ingredient of the general formula I in order to render possible the administration of daily doses of between 1.0 and 1000 mg/kg, preferably between 2 and 100 mg/kg, particularly between 5 and 10 mg/kg, to warm-blooded animals having a body weight of about 70 kg. Tablets and dragée cores are produced by combining the compounds of the formula I with solid pulverulent carriers, such as lactose, saccharose, sorbitol, maize starch, potato starch or amylopectin, cellulose derivatives or gelatine, preferably with the addition of lubricants, such as magnesium or calcium stearate, or polyethylene glycols of suitable molecular weight. Dragée cores are subsequently coated for example with concentrated sugar solutions which can also contain for example gum arabic, talcum and/or titanium dioxide, or with a lacquer dissolved in readily volatile organic solvents or solvent mixtures. Colouring agents may be added to these coatings, for example for identification of the various dosage amounts. Soft gelatine capsules and other closed capsules consist for example of a mixture of gelatine and glycerin, and can contain for example mixtures of a compound of the formula I with polyethylene glycol. Hard gelatine capsules contain for examples granulates of an active ingredient with solid pulverulent carriers, such as lactose, saccharose, sorbitol or mannitol; starches, such as potato starch, maize starch or amylopectin, cellulose derivatives as well as magnesium stearate or stearic acid.

Suitable dosage units for rectal administration are for example suppositories which consist of a combination of an active ingredient with a suppository foundation substance based on natural or synthetic triglycerides (for example cocoa butter), polyethylene glycols or suitable higher fatty alcohols; and gelatine rectal capsules which contain a combination of the active ingredient with polyethylene glycols.

For liquids to be taken orally, such as syrups and elixiers, the concentration of active ingredient is chosen to ensure that a single dose can be easily measured out, for example as the content of a tea-spoon or of a measuring spoon, for example 5 ml, or as a multiple of these amounts.

The following Examples (a) to (e) are intended to illustrate some typical forms of application, but in no way do they represent the only embodiments thereof.

(a) 100.0 g of active ingredient are mixed with 610.0 g of lactose and 442.0 g of potato starch; the mixture is then moistened with an alcoholic solution of 8 g of gelatine, and is granulated through a sieve. The granulate is dried, and 60.0 g of talcum, 10.0 g of magneseum stearate and 20.0 g of colloidal silicon dioxide are mixed in; and the mixture is subsequently pressed to form 10,000 tablets, each weighing 125 mg and each containing 10 mg of active ingredient. The tablets can, if desired, be provided with grooves for a more precise adjustment of the dosage amount.

(b) A granulate is prepared from 100.0 g of active ingredient, 379.0 g of lactose and the alcoholic solution of 6.0 g of gelatine; after drying, the granulate is mixed with 10.0 g of colloidal silicon dioxide, 40.0 g of talcum, 60.0 g of potato starch and 5.0 g of magnesium stearate, and the mixture is compressed to form 10,000 dragée cores. These are subsequently coated with a concentrated syrup prepared from 533.5 g of crystallised saccharose, 20.0 g of shellac, 75.0 g of gum arabic, 250.0 g of talcum, 20.0 g of colloidal silicon dioxide and 1.5 g of colouring agent, and finally dried. The dragées obtained each weigh 150 mg and each contain 10 mg of active ingredient.

(c) 10.0 g of active ingredient and 1990 g of finely ground suppository foundation substance (for example cocoa butter) are thoroughly mixed and then melted. The melt is maintained homogeneous by stirring whilst 1000 2.0 g suppositories each containing 25 mg of active ingredient are being poured.

(d) To prepare a syrup having a content of active ingredient of 0.25%, there are dissolved in 3 liters of distilled water 1.5 liters of glycerin, 42 g of p-hydroxybenzoic acid methyl ester, 18 g of p-hydroxybenzoic acid-n-propyl ester and, with slight warming, 25.0 g of active ingredient; to this solution are then added 4 liters of 70% sorbitol solution, 1000 g of crystallised saccharose, 350 g of glucose and an aroma substance, for example 250 g of "Orange Peel Soluble Fluid", Eli Lilly and Co., Indianapolis, or 5 g of natural lemon aroma and 5 g of "half and half" essence, both from Haarmann and Reimer, Holzminden, Germany; the solution obtained is filtered, and the filtrate is subsequently made up with distilled water to 10 liters.

(e) To prepare a drip solution containing 1.5% of active ingredient, 150.0 g of active ingredient and 30 g of sodium cyclamate are dissolved in a mixture of 4 liters of ethanol (96%) and 1 liter of propylene glycol. A mixture of 3.5 liters of 70% sorbitol solution and 1 liter of water is prepared separately and is then added to the above solution of active ingredient. An aroma substance, for example 5 g of cough-sweet aroma or 30 g of grapefruit essence, both from Haarmann and Reimer, Holzminden, Germany, is added; the whole is well mixed, filtered, and made up with distilled water to 10 liters.

The Examples which follow further illustrate the production of the novel compounds of the formula I, but in no way do they limit the scope of the invention. The temperature values are in degrees Centigrade.

EXAMPLE 1

11.2 g of 4-(3-cyano-4-morpholino-benzoyl)-butyrolactone together with 2.55 ml of hydrazine hydrate and 170 ml of ethanol are refluxed for 16 hours.

There are then added 29.7 ml of glacial acetic acid, and refluxing is maintained for a further 5 hours. The reaction mixture is subsequently cooled with stirring to room temperature, and the crystals which have precipitated are filtered off with suction and are washed with a small amount of ethanol and diethyl ether. The yield is 5.6 g of 6-(3-cyano-4-morpholino-phenyl)-5-hydroxymethyl-4,5-dihydro-3(2H)-pyridazinone, m.p. 217°–218° C.

The 4-(3-cyano-4-morpholino-benzoyl)-butyrolactone used as starting material is produced as follows:

10 g of 3-(3-cyano-4-morpholino-benzoyl)-propionic acid are stirred together with 2.98 g of 35% formaldehyde solution and 76.4 ml of 0.5N sodium hydroxide solution for 16 hours at room temperature. The reaction mixture, whilst being cooled with ice-water and stirred, is then rendered acid with concentrated hydrochloric acid, and is stirred for a further 16 hours at room temperature. Ethyl acetate is afterwards added until two clear phases are formed; the aqueous phase is subsequently separated, and extracted with ethyl acetate. The organic phases are washed twice with 2N sodium carbonate solution, with water and with brine; they are then dried over sodium sulfate and concentrated by evaporation. The 4-(3-cyano-4-morpholino-benzoyl)-butyrolactone obtained as an oily residue is used directly in the following stage.

EXAMPLE 2

From 3-(3-chloro-4-morpholino-benzoyl)-propionic acid is obtained 6-(3-chloro-4-morpholino-phenyl)-5-hydroxymethyl-4,5-dihydro-3(2H)-pyridazinone, m.p. 176°–178° C., and from 3-(3-nitro-4-morpholino-benzoyl)-propionic acid is obtained 6-(3-nitro-4-morpholino-phenyl)-5-hydroxymethyl-4,5-dihydro-3(2H)-pyridazinone, m.p. 216°–217° C., the procedure used being analogous to that described in Example 1.

EXAMPLE 3

1 g of 6-(3-cyano-4-morpholino-phenyl)-5-hydroxymethyl-4,5-dihydro-3(2H)-pyridazinone is stirred together with 0.3 ml of acetic anhydride, 0.66 ml of triethylamine, 20 ml of chloroform and 20 ml of dimethylformamide for 25 hours at 70° C., additions each of 0.3 ml of acetic anhydride being made after 5 hours and after 20 hours. The reaction mixture is evaporated to dryness, and the residue is chromatographed on silica gel in the system ethyl acetate:methanol=99:1. There is thus obtained 1 g of 6-(3-cyano-4-morpholino-phenyl)-5-acetoxymethyl- 4,5-dihydro-3(2H)-pyridazinone as an amorphous solid (foam) having a melting point of 60°–69° C. ($R_f$ in the system ethyl acetate:methanol=9:1 is 0.48).

EXAMPLE 4

45 g of 3-chloro-4-amino-benzoyl-propionic acid are stirred together with 50 ml of 35% formaldehyde solution and 440 ml of 0.5N sodium hydroxide solution for 17 hours at room temperature. The reaction mixture is adjusted with 2N hydrochloric acid to pH 5, and is extracted with ethyl acetate. The ethyl acetate phases are washed with water, dried over sodium sulfate and concentrated by evaporation. The residue, 3-(3-chloroamino-benzoyl)-3-hydroxymethyl)-propionic acid, is directly further reacted unpurified by being refluxed together with 1600 ml of ethanol and 18 ml of hydrazine hydrate for 5 hours. The reaction mixture is concentrated by evaporation, and the residue is distributed between 4N hydrochloric acid and ethyl acetate. The aqueous phases are rendered basic with a 2N sodium carbonate solution, and are extracted with ethyl acetate. The ethyl acetate extracts are washed twice with 2N sodium carbonate solution and with water, dried and then concentrated by evaporation. As residue is obtained the crude 6-(3-chloro-4-amino-phenyl)-5-hydroxymethyl-4,5-dihydro-3(2H)-pyridazinone, which together with 25 g of $\beta,\beta$-dibromodiethyl ether and 37 ml of diisopropylethylamine in 150 ml of dimethylformamide are refluxed for 18 hours. The reaction mixture is concentrated under high vacuum in a rotary evaporator; the residue is then taken up in ethyl acetate, and repeatedly washed with 1N hydrochloric acid and water. The organic phase is dried over sodium sulfate and concentrated by evaporation, the product which crystallises out being 6-(3-chloro-4-morpholino-phenyl)-5-hydroxymethyl-4,5-dihydro-3(2H)-pyridazinone, m.p. 172°–173° C.

EXAMPLE 5

26.3 g of p-morpholino-benzoyl-propionic acid are stirred together with 25 ml of a 35% formaldehyde solution and 220 ml of 0.5N sodium hydroxide solution for 18 hours at room temperature. The reaction mixture is adjusted with 2N hydrochloric acid to pH 3, and is extracted with ethyl acetate. The ethyl acetate phases are washed with water, dried over sodium sulfate and concentrated by evaporation. The residue, crude 3-(p-morpholino-benzoyl)-3-hydroxymethyl-propionic acid, is refluxed together with 9 ml of hydrazine hydrate and 800 ml of ethanol for 5 hours. The reaction mixture is afterwards concentrated in the rotary evaporator. The residue is taken up in ethyl acetate; the organic phases are then repeatedly washed with 2N sodium carbonate solution and with water, dried over sodium sulfate, and concentrated by evaporation. The residue is chromatographed on silica gel with a mixture of ethyl acetate:methanol=9:1. The 6-(4-morpholino-phenyl)-5-hydroxymethyl-4,5-dihydro-3-(2H)-pyridazinone thus obtained is dissolved in a mixture of 16 ml of glacial acetic acid and 20 ml of concentrated hydrochloric acid, and there is then added at −10° C., with stirring, the solution of 1.8 g of sodium chlorate in 2 ml of water. The mixture is further stirred for 30 minutes at 0° C. and for 30 minutes at room temperature, and is subsequently poured into 400 ml of ice-water. The suspension thus formed is adjusted with concentrated NaOH to pH 6, and then extracted with ethyl acetate. The ethyl acetate extracts are washed with a 1N sodium bicarbonate solution and with water, dried over sodium sulfate and concentrated by evaporation. The residue is purified on silica gel with a mixture of ethyl acetate: methanol=9:1. Recrystallisation of the corresponding fractions from ethyl acetate yields 6-(3-chloro-4-morpholino-phenyl)-5-hydroxymethyl-4,5-dihydro-3(2H)-pyridazinone, m.p. 173°–175° C.

EXAMPLE 6

10 g of 6-(3-nitro-4-morpholino-phenyl)-5-hydroxymethyl-4,5-dihydro-3(2H)-pyridazinone are hydrogenated with 1g of palladium-on-charcoal catalyst in 200 ml of ethanol at room temperature and under low pressure. For processing, the catalyst is suspended in 1N hydrochloric acid, filtered off with suction, and subsequently washed with 1N hydrochloric acid. The filtrate is adjusted with 2N sodium hydroxide solution to pH 6, and is extracted with ethyl acetate. The organic phases are washed with brine, dried over sodium sulfate and concentrated by evaporation. The residue, crude 6-(3-amino-4-morpholino-phenyl)-5-hydroxymethyl-4,5-dihydro-3(2H)-pyridazinone, is dissolved in a mixture of 90 ml of concentrated hydrochloric acid and 90 ml of water, and the solution is diazotised at 0°–5° C., while stirring is maintained, with the solution of 2.9 g of sodium nitrite in 10 ml of water, the excess nitrite being destroyed after 15 minutes with urea. There is then quickly added the solution of 18 ml of copper(I) chloride in a mixture of 90 ml of water and 90 ml of concentrated hydrochloric acid. After completion of the addition, the reaction mixture is further stirred for 3 hours at room temperature and for 2 hours at 40° C.; it is subsequently adjusted to pH 10 and extracted with ethyl acetate. The ethyl acetate phases are washed with water and with brine, dried over sodium sulfate and concentrated by evaporation. The residue is purified on silica gel with a mixture of ethyl acetate:methanol=9:1, and then recrystallised from ethyl acetate to thus obtain 6-(3-chloro-4-morpholinophenyl)- 5-hydroxymethyl-4,5-dihydro-3(2H)-pyridazinone, m.p. 174°–176° C.

EXAMPLE 7

25 g of 3-nitro-4-chloro-benzoyl-propionic acid are stirred together with 25 ml of a 35% formaldehyde solution and 220 ml of 0.5N sodium hydroxide solution for 16 hours at room temperature. The reaction mixture is adjusted with 2N hydrochloric acid to pH 3, and is extracted with ethyl acetate. The ethyl acetate phases are washed with water, dried over sodium sulfate and concentrated by evaporation. The 3-(3-nitro-4-chlorobenzoyl)-3-hydroxymethyl-propionic acid obtained as residue is refluxed together with 9 ml of hydrazine hydrate and 800 ml of ethanol for 5 hours. The reaction mixture is afterwards concentrated by evaporation, and the residue is stirred together with 170 ml of dimethyl sulfoxide, 10 ml of morpholine and 15 ml of diisopropylethylamine for 3 hours at 80° C. The reaction mixture is subsequently concentrated under high vacuum in a rotary evaporator, and the residue is refluxed in 90 ml of methylene chloride for 30 minutes. The product which crystallises out on cooling of the reaction mixture with stirring to 0° C. is 6-(3-nitro-4-morpholino-phenyl)-5-hydroxymethyl-4,5-dihydro-3(2H)-pyridazinone, m.p. 210°–213° C.

EXAMPLE 8

The solution of 5 g of 3-(3-cyano-4-morpholinobenzoyl)-propionic acid in 50 ml of dimethylformamide is added dropwise to a solution of 1.66 ml of a sodium hydride dispersion in 50 ml of dimethylformamide. The reaction mixture is stirred at 70° C. for 30 minutes, and there are then added dropwise at −70° C., with stirring, 7.2 ml of benzyl-chloromethyl ether. Stirring is continued for 1 hour at −70° C. and for 16 hours at room temperature. There are subsequently added successively 30 ml of water, 10 ml of 2N hydrochloric acid and 50 ml of water; the mixture is afterwards extracted with ether, and the ether phases, after being washed with water and dried over sodium sulfate, are concentrated by evaporation. The residue together with 4 ml of hydrazine hydrate and 200 ml of 50% acetic acid is stirred for 2 hours at 100° C. and for 16 hours at room temperature. The mixture is concentrated in a rotary evaporator, and the residue is taken up in ethyl acetate.

The organic phases are washed with water, with 1N sodium bicarbonate solution and with brine, dried over sodium sulfate and concentrated by evaporation. There is obtained from the residue, by chromatography on silica gel with a mixture of toluene: ethyl acetate=1:1, 6-(3-cyano-4-morpholino-phenyl)-5-benzyloxymethyl-4,5-dihydro-3(2H)-pyridazinone, m.p. 156°–167° C.

1 g of 6-(3-cyano-4-morpholino-phenyl)-5-benzyloxymethyl-4,5-dihydro-3(2H)-pyridazinone is hydrogenated in 100 ml of ethanol with 0.3 g of a palladium-on-charcoal catalyst. The catalyst is filtered off with suction and the filtrate is concentrated by evaporation. The residue is refluxed in 8 ml of methylene chloride for 30 minutes and then cooled to 0° C. The product crystallising out while stirring is maintained is 6-(3-cyano-4-morpholinophenyl)-5-hydroxymethyl-4,5-dihydro-3(2H)-pyridazinone. The melting point after recrystallisation from ethanol/dimethylformamide is 219°–221° C.

EXAMPLE 9

86.5 g of 3-(3-cyano-4-morpholino-benzoyl)-propionic acid are stirred together with 79 ml of a 35% formaldehyde solution and 660 ml of 0.5N sodium hydroxide solution for 17 hours at room temperature. The pH value is afterwards adjusted to 3 with 160 ml of 2N hydrochloric acid, and the mixture is extracted with ethyl acetate. The organic phases are dried with sodium sulfate, and concentrated by evaporation. The residue is stirred together with 28 ml of hydrazine hydrate and 2850 ml of ethanol for 5 hours under refluxing conditions, and the mixture is subsequently concentrated in a rotary evaporator. The residue is suspended in 900 ml of methylene chloride, and the suspension is refluxed for 30 minutes. The product which crystallises out on cooling to 0° C. is 6-(3-cyano-4-morpholino-phenyl)-5-hydroxymethyl-4,5-dihydro-3(2H)-pyridazinone, m.p. 213°–215° C. As a result of recrystallisation from 400 ml of methylene chloride with 400 ml of ethanol, the melting point rises to 221°–222° C.

What is claimed is:

1. A pyridazinone of the general formula I

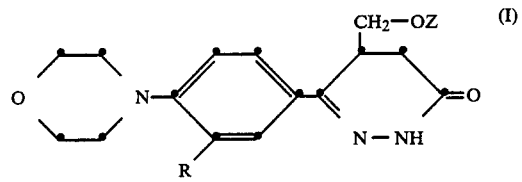

wherein R is a halogen atom, a lower alkyl or lower alkoxy group, the nitro, hydroxyl, cyano, carboxyl, lower alkoxycarbonyl or carbamoyl group or the trifluoromethyl group, and Z is hydrogen or an acyl group, and the salts and tautomeric forms thereof.

2. A pyridazinone of the general formula I given in claim 1, wherein R is a halogen atom, or the cyano, hydroxyl, carboxyl, lower alkyl or lower alkoxy group or the trifluoromethyl group, and Z is hydrogen or lower alkanoyl, and the salts and tautomeric forms thereof.

3. A pyridazinone of the general formula I given in claim 1, wherein R is a halogen atom, especially chlorine, a lower alkyl group, particularly methyl, or the cyano group, and Z is hydrogen or lower alkanoyl, in particular acetyl, and the tautomeric forms thereof.

4. A compound according to claim 3, which is 6-(3-cyano-4-morpholino-phenyl)-5-hydroxymethyl-4,5- dihydro-3(2H)-pyridazinone, and the tautomeric forms thereof.

5. A compound according to claim 3, which is 6-(3-chloro-4-morpholino-phenyl)-5-hydroxymethyl-4,5-dihydro-3(2H)-pyridazinone, and the tautomeric forms thereof.

6. A compound according to claim 3, which is 6-(3-nitro-4-morpholino-phenyl)-5-hydroxymethyl-4,5-dihydro-3(2H)-pyridazinone, and the tautomeric forms thereof.

7. A compound according to claim 3, which is 6-(3-cyano-4-morpholino-phenyl)-5-acetoxymethyl-4,5-dihydro-3(2H)-pyridazinone, and the tautomeric forms thereof.

8. A therapeutic composition for the treatment of thrombotic diseases comprising an effective amount of an antithrombotic active compound of formula I as claimed in claim 1 together with a pharmaceutically acceptable excipient.

9. A therapeutic composition as defined in claim 8, wherein the antithrombotic active compound is 6-(3-cyano-4-morpholino-phenyl)-5-hydroxymethyl-4,5-dihydro-3(2H)-pyridazinone or a tautomeric form thereof.

10. A method for the treatment of thrombotic diseases, which comprises administering to a living body suffering from thrombotic diseases an effective amount of a compound of formula I as claimed in claim 1.

* * * * *